(12) United States Patent
Wirjadi et al.

(10) Patent No.: US 11,735,306 B2
(45) Date of Patent: Aug. 22, 2023

(54) METHOD, SYSTEM AND COMPUTER READABLE STORAGE MEDIA FOR CREATING THREE-DIMENSIONAL DENTAL RESTORATIONS FROM TWO DIMENSIONAL SKETCHES

(71) Applicant: DENTSPLY SIRONA INC., York, PA (US)

(72) Inventors: Oliver Wirjadi, Frankfurt (DE); Behrang Shafei, Heppenheim (DE)

(73) Assignee: DENTSPLY SIRONA INC., York, PA (US)

( * ) Notice: Subject to any disclaimer, the term of this patent is extended or adjusted under 35 U.S.C. 154(b) by 821 days.

(21) Appl. No.: 16/693,902

(22) Filed: Nov. 25, 2019

(65) Prior Publication Data
US 2021/0153986 A1    May 27, 2021

(51) Int. Cl.
| | | |
|---|---|---|
| G16H 20/30 | (2018.01) | |
| A61C 7/00 | (2006.01) | |
| A61C 9/00 | (2006.01) | |
| A61C 13/00 | (2006.01) | |
| G06N 3/04 | (2023.01) | |
| G06T 17/10 | (2006.01) | |
| G06F 18/214 | (2023.01) | |

(52) U.S. Cl.
CPC ............. *G16H 20/30* (2018.01); *A61C 7/002* (2013.01); *A61C 9/0053* (2013.01); *A61C 13/0004* (2013.01); *A61C 13/0019* (2013.01); *G06F 18/214* (2023.01); *G06N 3/04* (2013.01); *G06T 17/10* (2013.01)

(58) Field of Classification Search
CPC ... A61C 13/0007; A61C 7/002; A61C 9/0053; A61C 13/0019; G06K 9/6256; G06N 3/04; G06T 17/10
See application file for complete search history.

(56) References Cited

U.S. PATENT DOCUMENTS

| | | |
|---|---|---|
| 6,711,293 B1 | 3/2004 | Lowe |
| 7,583,272 B2 | 9/2009 | Ramani |
| 7,592,272 B2 | 9/2009 | Tonomura |
| 8,982,147 B2 | 3/2015 | Ramani |
| 9,336,336 B2 | 5/2016 | Deichmann |

(Continued)

FOREIGN PATENT DOCUMENTS

| | | |
|---|---|---|
| CA | 3054100 A1 | 9/2018 |
| CN | 100456300 C | 1/2009 |

(Continued)

OTHER PUBLICATIONS

International Search Report; PCT/US2020/051976; Dec. 4, 2020 (completed); dated Dec. 15, 2020.

(Continued)

*Primary Examiner* — Nicholas D Lucchesi
(74) *Attorney, Agent, or Firm* — Dentsply Sirona Inc.

(57) ABSTRACT

A method, system and computer readable storage media for obtaining 3D dental restoration geometries from 2D dental designs. This may include obtaining a training dataset, training the neural network using the training dataset, taking a scan of a patient, such as a 3D measurement of a patient's oral cavity, obtaining a 2D dental design, producing a 3D dental restoration geometry using the obtained 2D dental design and the trained neural network.

20 Claims, 9 Drawing Sheets

(56) References Cited

U.S. PATENT DOCUMENTS

| | | | |
|---|---|---|---|
| 9,672,444 B2 | 6/2017 | Mehl | |
| 9,788,917 B2 | 10/2017 | Mah | |
| 2013/0218531 A1 | 8/2013 | Fisker | |
| 2018/0028294 A1 | 2/2018 | Azernikov | |
| 2018/0374245 A1* | 12/2018 | Xu | G06T 11/005 |
| 2019/0026893 A1 | 1/2019 | Salah | |
| 2019/0282344 A1* | 9/2019 | Azernikov | G06F 30/00 |
| 2019/0313963 A1* | 10/2019 | Hillen | A61B 5/7475 |
| 2020/0349698 A1* | 11/2020 | Minchenkov | G06T 19/20 |
| 2021/0110605 A1* | 4/2021 | Haslam | B33Y 50/00 |
| 2021/0346091 A1* | 11/2021 | Haslam | A61B 34/10 |
| 2021/0353393 A1* | 11/2021 | Kearney | A61B 5/0088 |
| 2022/0047160 A1* | 2/2022 | Yoo | G16H 50/70 |

FOREIGN PATENT DOCUMENTS

| | | | |
|---|---|---|---|
| WO | 200906303 A2 | 1/2009 | |
| WO | 201200511 A1 | 1/2012 | |
| WO | 201207003 A1 | 1/2012 | |

OTHER PUBLICATIONS

Written Opinion of the International Searching Authority; PCT/US2020/051976; Dec. 4, 2020 (completed); dated Dec. 15, 2020.
International Preliminary Report on Patentability; PCT/US2020/051976; Dec. 4, 2020 (completed); dated Dec. 15, 2020.
Jiaxin Chen et al; "Deep Cross-modality Adaptation via Semantics Preserving Adversarial Learning for Sketch-based 3D Shape Retrieval"; Computer Vision Foundation; 2018; pp. 1-16.

\* cited by examiner

METHOD, SYSTEM AND COMPUTER READABLE STORAGE MEDIA FOR CREATING THREE-DIMENSIONAL DENTAL RESTORATIONS FROM TWO DIMENSIONAL SKETCHES

FIELD OF THE INVENTION

The present application relates generally to a method, a system and computer readable storage media for generating three-dimensional (3D) models of dental restorations and, more particularly, to a method, system and computer readable storage media for generating 3D dental restoration geometries in an overall 3D model, with the geometries corresponding to 2D dental designs that have desired/defined constraints.

BACKGROUND OF THE INVENTION

Dental restorations are produced by means of CAD/CAM-systems. These CAD/CAM-systems may allow for the 3D-design of a dental restoration using a software. The creation of such restorations with very specific properties demanded by the dental professional operating the digital workflow may not be optimal in terms of usability.

In order to achieve desired aesthetics for a patient, some systems may allow users to view the result of a 3D-design/restoration in relation to the patient's photographs. Said 3D-design may be algorithmically projected onto a plane/rendered to produce a 2D image in which the restorations designed in software can be seen in relation to the patient's face. This workflow is often referred to as "smile design".

A problem with these existing approaches is that it requires modification of the 3D design after visualizing the 2D result. A "forward approach" may start from designing tooth outlines in a photograph by taking into consideration features such as positions of eyes and nose, lips and lip support, and producing a 3D restoration proposal based on those features.

For a restoration a user may desire specific properties of the tooth's geometry and the process of obtaining this may be lengthy and cumbersome. For instance, he or she may want to restore a molar with a particularly formed fissure. With current solutions he either has to select the tooth from a database, use a variation slider, rely on proposals, use CAD-tools manually, and/or apply manual post-processing on a produced restoration. A way to automatically generate a proposal that incorporates the desired features of a user and saves time is therefore needed.

U.S. patent application Ser. No. 13/809,797 discloses a method for the 3D modeling of an object using textural features wherein the 3D modeling may apply information of one or more features from an acquired 2D digital representation including textural data of the location where a 3D object is adapted to be arranged. The 2D digital representation comprising textural data and a 3D digital representation comprising geometrical data may be aligned and combined to obtain a combined 3D digital representation.

U.S. Pat. Nos. 8,982,147, 7,583,272 disclose a search of a database comprising 2D or 3D representations of objects using at least one graphical input parameter, wherein said graphical input parameter may be a 2D or a 3D representation of all or part of an object.

A publication "Deep Gross-modality Adaptation via Semantics Preserving Adversarial Learning for Sketch-based 3D Shape Retrieval" by Jiaxin Chen, Yi Fang; ECCV 2018, pp. 605-620, teaches a neural network that may retrieve a 3D geometry from a database, wherein the 3D geometry corresponds to a given a 2D sketch input. In said publication, the system relies heavily on said database to produce 3D results.

Chinese Patent No. CN100456300C discloses a method for retrieving a 3D model from a database based on a 2D sketch.

U.S. Pat. No. 9,336,336 discloses a method for designing a dental restoration by providing one or more 2D images, providing a 3D virtual model of at least part of a patient's oral cavity, arranging at least one of the one or more 2D images relative to the 3D virtual model in a virtual 3D space such that the 2D image and the 3D virtual model are aligned when viewed from a viewpoint, and modeling a restoration on the 3D virtual model, where the restoration to fit the facial feature of the at least one 2D image.

U.S. Pat. No. 9,788,917B2 discloses a method for employing artificial intelligence in automated orthodontic diagnosis and treatment planning. The method may include providing an intraoral imager configured to be operated by a patient; receiving patient data regarding the orthodontic condition; accessing a database that comprises or has access to information derived from orthodontic treatments; generating an electronic model of the orthodontic condition; and instructing at least one computer program to analyze the patient data and identify at least one diagnosis and treatment regimen of the orthodontic condition based on the information derived from orthodontic treatments.

U.S. Patent Application Publication No. 20190026893A1 discloses a method for assessing the shape of an orthodontic aligner wherein an analysis image is submitted to a deep learning device, in order to determine a value of a tooth attribute relating to a tooth represented on the analysis image, and/or at least one value of an image attribute relating to the analysis image.

U.S. Application Publication No. 20180028294A1 discloses a method for Dental CAD Automation using deep learning. The method may include receiving a patient's scan data representing at least one portion of the patient's dentition data set; and identifying, using a trained deep neural network, one or more dental features in the patient's scan. Herein, design automation may be carried out after complete scans have been generated.

SUMMARY OF THE INVENTION

Existing limitations associated with the foregoing, as well as other limitations, can be overcome by a method, system and computer readable storage media for utilizing deep learning methods to produce 3D dental restoration geometries with the geometries corresponding to 2D dental designs that have desired/defined constraints.

In an aspect herein, the present invention may provide a computer implemented method for producing a three-dimensional (3D) dental restoration geometry from a two-dimensional (2D) dental design, the method comprising: receiving, by one or more computing devices, the 2D dental design having design constraints that represent defined properties of said 3D dental restoration geometry; using a first trained neural network to convert the 2D dental design into a latent representation that has information about said defined properties of the 3D dental restoration geometry; upsampling the latent representation to automatically generate the 3D dental restoration geometry by using the latent representation as input to a second trained neural network and converting said latent representation into a 3D shape that has corresponding properties that adhere to said design constraints.

In another aspect herein, the computer implemented method may further comprise one or more combinations of the following steps: (i) adapting the 3D dental restoration into a final digital dental restoration to fit inside a patient's oral cavity based on anatomical constraints obtained from 3D scans of the patient; (ii) wherein the defined properties include cusps, ridges, fissures, bifurcations, tooth shape and tooth texture; (iii) wherein the first neural network is a convolutional neural network; (iv) wherein the second neural network is (a) hybrid solution such an additional neural network selected from a convolutional neural network, a recurrent neural network, and a fully connected multilayer perceptron or wherein the second neural network is (b) an end-to-end learning model such as a three-dimensional generative adversarial neural network (3D-GAN); (v) using an output of the said hybrid solution/additional neural network as an input to a parametric model wherein the convolutional neural network has a same number of input units as a length of the latent representation, and another same number of output units as the number of input parameters of the parametric model; (vi) wherein the 3D dental restoration geometry is generated as a 3D triangular mesh or a 3D rasterized data; (vii) wherein the 2D dental designs are 2D sketches recorded in an analog or digital way; (viii) manufacturing a physical dental restoration from the final digital dental restoration using a computer-aided design/computer-aided manufacturing (CAD/CAM) system; (ix) training the first and second neural networks using the one or more computing devices and a plurality of training images in a training dataset, to map a 2D training image having design constraints to a 3D training image, wherein the first neural network is trained to convert the 2D training image into a latent representation that has information about defined properties of the 3D training image, and the second neural network is trained to upsample the latent representation to automatically generate the 3D training image such that is has corresponding properties that adhere to said design constraints of said 2D training image; (x) re-training the first and second neural networks using 2D training images of a specific user in order to subsequently generate 3D dental restoration geometries that match or substantially match said user's drawing style.

In an aspect herein, the present invention may provide a non-transitory computer-readable storage medium storing a program which, when executed by a computer system, causes the computer system to perform a procedure comprising: receiving, by one or more computing devices, a two-dimensional (2D) dental design having design constraints that represent defined properties of said 3D dental restoration geometry; using a first trained neural network to convert the 2D dental design into a latent representation that has information about said defined properties of the 3D dental restoration geometry; upsampling the latent representation to automatically generate the 3D dental restoration geometry by using the latent representation as input to a second trained neural network and converting said latent representation into a 3D shape that has corresponding properties that adhere to said design constraints.

In a further aspect herein, the present invention may provide a system for producing a three-dimensional (3D) dental restoration geometry from a two-dimensional (2D) dental design, the system comprising a processor configured to: receive, by one or more computing devices, the 2D dental design having design constraints that represent defined properties of said 3D dental restoration geometry; use a first trained neural network to convert the 2D dental design into a latent representation that has information about said defined properties of the 3D dental restoration geometry; upsample the latent representation to automatically generate the 3D dental restoration geometry by using the latent representation as input to a second trained neural network and converting said latent representation into a 3D shape that has corresponding properties that adhere to said design constraints.

In another aspect herein, the system may further comprise one or more combinations of the following features: (i) the processor is further configured to adapt the 3D dental restoration into a final digital dental restoration to fit inside a patient's oral cavity based on anatomical constraints obtained from 3D scans of the patient; (ii) the first neural network is a convolutional neural network; (iii) the second neural network is a hybrid solution such as an additional neural network selected from a convolutional neural network, a recurrent neural network, and a fully connected multilayer perceptron or wherein the second neural network is an end-to-end learning model such as a three-dimensional generative adversarial neural network (3D-GAN); (iv) the 3D dental restoration geometry is a 3D triangular mesh or a 3D rasterized data; (v) the 2D dental designs are 2D sketches recorded in an analog or digital way.

In an even further aspect herein, the present invention may provide another computer implemented method for producing a three-dimensional (3D) dental restoration geometry from one or more two-dimensional (2D) dental designs, the method comprising: receiving, by one or more computing devices, the one or more 2D dental designs having design constraints that represent defined properties of said 3D dental restoration geometry; using a first trained neural network to convert the one or more 2D dental designs into a latent representation that has information about said defined properties of the 3D dental restoration geometry; upsampling the latent representation to automatically generate the 3D dental restoration geometry by using the latent representation as input to a second trained neural network and converting said latent representation into a 3D shape that has corresponding properties that adhere to said design constraints.

In yet another aspect herein, the present invention may provide another computer implemented method for producing one or more three-dimensional (3D) dental restoration geometries from a two-dimensional (2D) dental design, the method comprising: receiving, by one or more computing devices, the 2D dental design that has design constraints that represent defined properties of said one or more 3D dental restoration geometries; using a first trained neural network to convert the 2D dental design into a latent representation that has information about said defined properties of the one or more 3D dental restoration geometries; upsampling the latent representation to automatically generate the one or more 3D dental restoration geometries by using the latent representation as input to a second trained neural network and converting said latent representation into a 3D shape that has corresponding properties that adhere to said design constraints.

Advantages may include the ability to upsample 2D-Data to 3D-Data since neural nets usually attempt to reduce high dimensional data (e.g.: Images, speech. Etc.) into a lower-dimensional (e.g. labels for objects in images, text etc.). Moreover the use of auto-encoders to replicate inputs is advantageous as 2D-inputs may be trained to fit to 3D targets. In contrast to other methods such as is described in the paper by Achlioptas et al (Learning Representations and Generative Models for 3D Point Clouds, published Jun. 12, 2018), training may be accomplished in one process instead of first training an auto-encoder, and then a GAN on top of that. Moreover, unlike in Achlioptas et al, translation may not necessarily be fixed to a pre-defined number of input points.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein and wherein.

Figure 1:
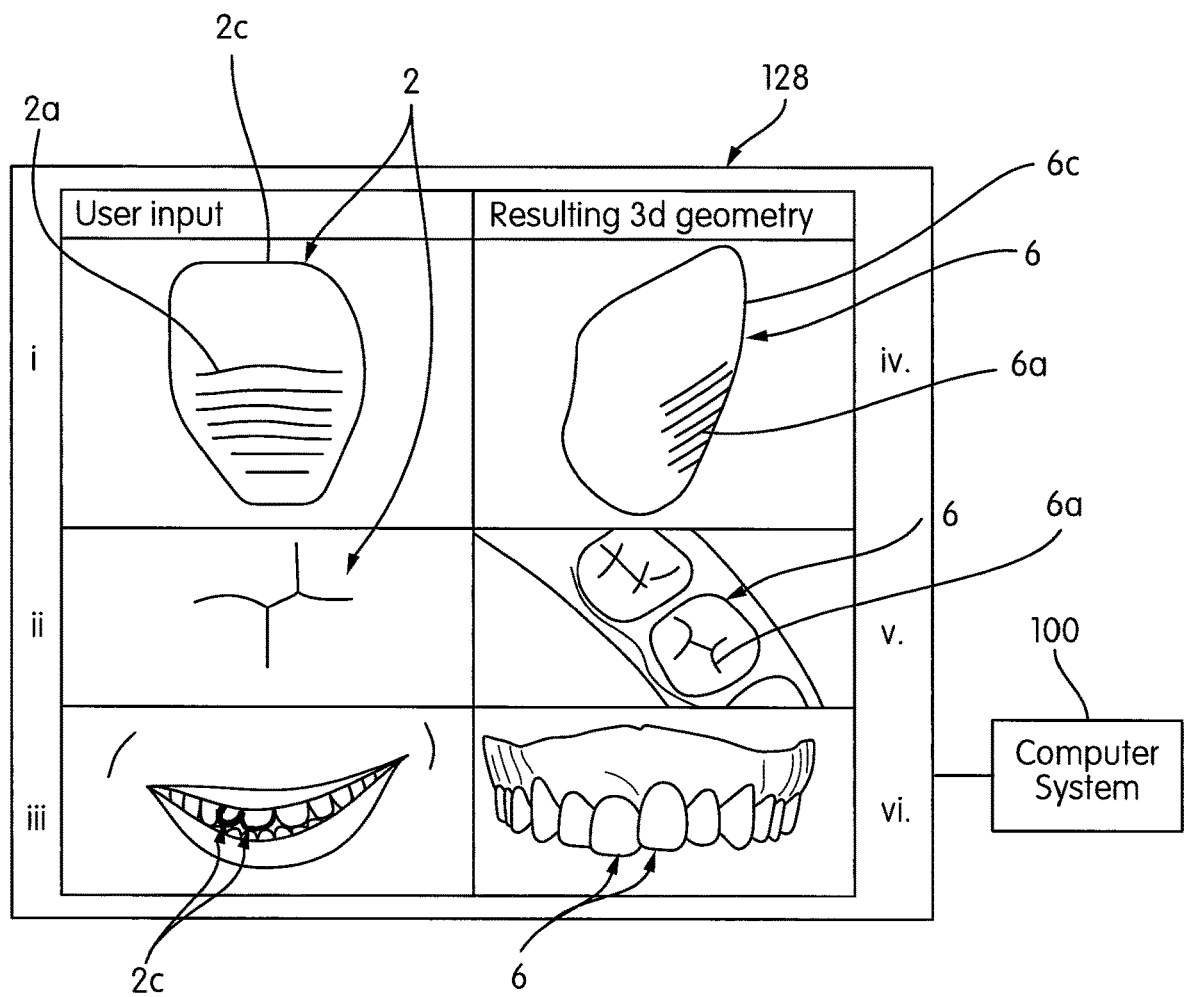
FIG. 1 is a sketch of a display unit illustrating 2D sketches and corresponding 3D dental restoration geometries.

Different ones of the figures may have at least some reference numerals that may be the same in order to identify the same components, although a detailed description of each such component may not be provided below with respect to each Figure.

DETAILED DESCRIPTION OF THE INVENTION

In accordance with example aspects described herein, a method, system and computer readable storage media may be provided for utilizing deep learning methods to generate 3D dental restoration models from 2D sketches.

System for Producing 3D Dental Restoration Geometries

The invention proposes a system 200 (FIG. 2) for translating 2D dental designs 2 (such as dental sketches), having design constraints (such as design features 2a and/or design outlines 2c, as shown in FIG. 1), into 3D dental restoration geometries 6 (which may preferably be represented as 3D triangular meshes) that have corresponding properties (preferably physical properties such as 3D features 6a and 3D outlines 6c) which adhere to said design constraints specified by a user. The 3D dental restoration geometries may also be quad meshes, grid/raster data (voxels), implicit functions, spline-based representations such as Bezier patches, extrusion surfaces, swept surfaces or the like. In an embodiment, the system may also translate 2D dental designs 2 into 3D dental restoration geometries 6 that adhere to anatomical constraints such as bite contacts, tooth positions on connecting elements (stumps, implants, etc.) that may be known to a dental CAD/CAM system through 3D scans such as intraoral or extra oral (e.g. impression scans or scans of stone models) patient scans 30 (FIG. 3) obtained from a dental camera 3. More specifically, a user may take a patient's anatomical constraints into consideration while producing the 2D dental designs 2 in order for the system to translate the 2D dental designs 2 into 3D dental restoration geometries 6 that fit the patient's intraoral cavity. Herein the system may be supplied with the 2D dental design 2 produced by a user taking into consideration the patient scans 30. Using a network trained with a plurality of training datasets of 2D dental designs, the system may produce 3D dental restoration geometries 6 that fit the patient's cavity.

Further, in another embodiment, the system itself may take the anatomical constraints into consideration in order to produce 3D dental restoration geometries 6 that fit the patient's cavity. Herein the system may be supplied with the patient scan 30 in addition to the 2D dental designs 2. Using a network trained with a plurality of training datasets of 3D patient scans as well as a plurality of training datasets of 2D dental designs, the system may produce 3D dental restoration geometries 6 that fit the patient's cavity.

A user may draw as input to the system 200, a 2D dental design 2 that may include defined properties for a 3D geometry of a tooth/teeth as illustrated in FIG. 1. This may be displayed on a display unit 128 which may be separate from a computer system 100 or part of the computer system 100. The 2D dental design 2 may be obtained by one of several ways such as through 2D human-made hand drawings that may be recorded in an analog or digital fashion. In an exemplary embodiment, the 2D dental design may be drawn directly on a touch screen display using an input unit such as stylus pen, a finger or the like. In another embodiment, a gesture recognition device may be used to obtain the drawing. In yet another embodiment, a picture of tooth may be used.

Further to the manual process of obtaining the 2D dental design 2, automated methods such as automatically generating a sketch through, for example, automatically analyzing the position, shape, size, and possible texture of a missing tooth in relation to other teeth in a patient's intra-oral cavity measurement and proposing a 2D dental design 2 that represents a replacement for the missing tooth, may be used. Moreover 2D pictures such as previously stored pictures in a database representing the tooth/teeth to be replaced may be automatically/manually selected to be used.

The obtained 2D dental designs 2 may represent certain desired properties of a restoration to-be-produced (including properties such as: fissure, bifurcations, cusps, ridges, tooth shape, textures on incisors, etc.) and may be in the form of grayscale, black/white or color images. These design constraints may represent and/or resemble real world features as seen on teeth. A neural network such as a deep neural network 300 (FIG. 4) may be trained according to one or more methods as described hereinafter, to output 3D dental restoration geometries 6 with corresponding 3D features 6a and/or outlines 6c that adhere to the design constraints (e.g. design features 2a and/or outlines 2c). In an embodiment herein, the 2D dental designs 2 may be RGB Images, grayscale images, black/white images etc. Drawing/producing such 2D dental designs may be more natural to users than producing 3D CAD designs.

The system 200 may therefore train neural networks such as deep neural networks, using a plurality of training data sets, to automatically recognize 2D dental designs 2 and create corresponding 3D dental restoration geometries, preferably in real time.

Figure 2:
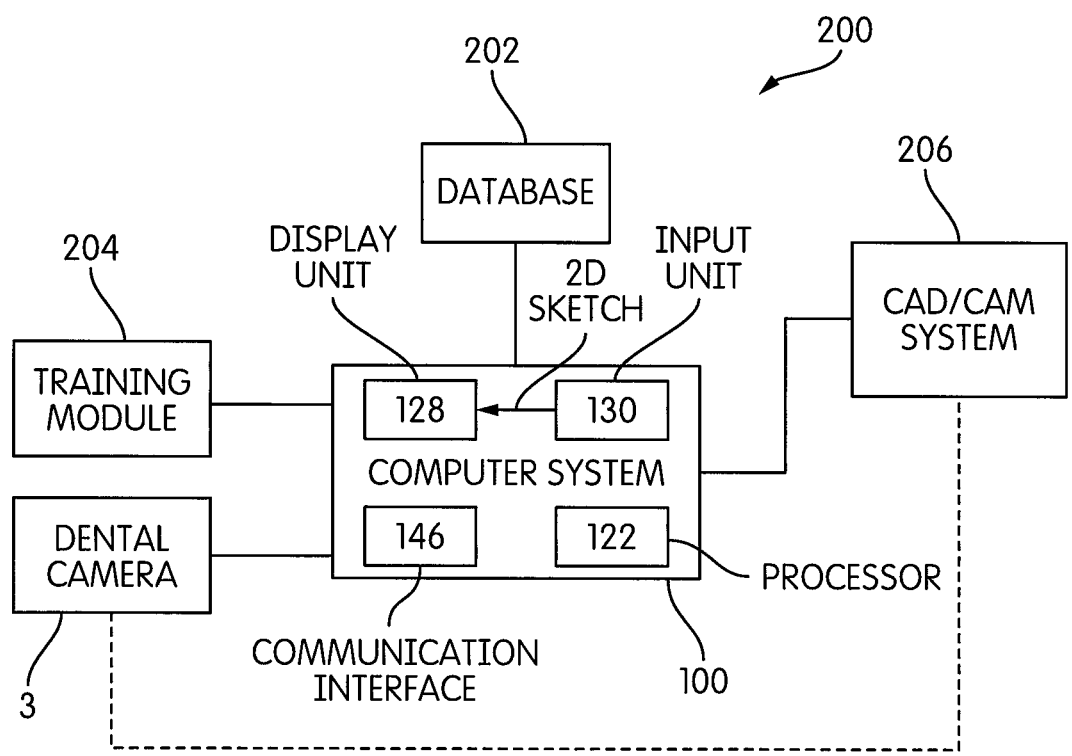
FIG. 2 is a high level block diagram of a system according to an embodiment of the present invention.
Figure 3:
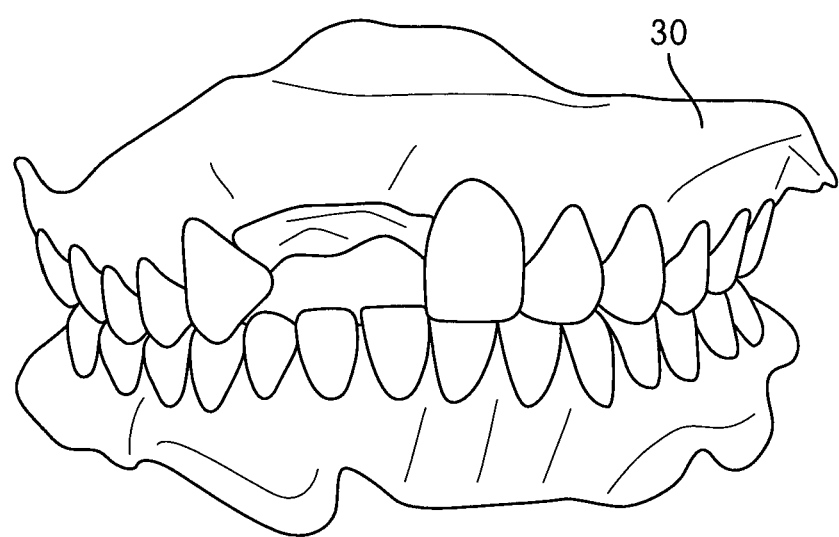
FIG. 3 is a front view of a scan of a patient's oral cavity illustrating missing teeth according to an embodiment of the present invention.

FIG. 2 shows a block diagram of the system 200 which may include a dental camera 3, a training module 204, CAD/CAM System 206, a computer system 100 and a database 202. In another embodiment, the database 202, CAD/CAM System 206, and/or training module 204 may be part of the computer system 100. The computer system 100 may also include at least one computer processor 122, the display unit 128 and input unit 130. The computer processor may receive various restoration requests to produce 3D dental restorations geometries as virtual 3D models and may load appropriate instructions, as stored on a storage device, into memory and then execute the loaded instructions. These instructions may include obtaining and using a 2D design as input to a neural network to obtain a 3D model as output. The computer system 100 may also include a communications interface 146 that enables software and data to be transferred between the computer system 100 and external devices.

Alternatively, the computer system may independently produce 3D dental restoration geometries 6 upon receiving 2D dental designs 2 and/or patient scans 30 that have missing teeth, without waiting for a request.

In one embodiment, the computer system 100 may use many training data sets from a database 202 (which may include, for example, a set of pairs of 2D-sketches/2D training images and corresponding 3D-restoration geometries/3D training meshes) to train one or more deep neural networks 300, which may be a part of training module 204. In an embodiment, a plurality of 2D training images may be mapped to a corresponding 3D dental restoration geometry. In another embodiment a 2D training image may be mapped to a plurality of 3D restoration geometries. In other embodiments, the system 200 may include a neural network module (not shown) that contains various deep neural networks such as Convolutional Neural Networks (CNN), 3D-generative adversarial networks (3D-GAN).

The training data sets and/or inputs to the neural networks may be pre-processed. For example, removal of outliers in the data, as well as data augmentation procedures such as synthetic rotations, scalings etc. may be applied to the training data sets and/or inputs.

The training module 204 may use training data sets to train the deep neural network in an unsupervised manner. In view of the descriptions provided herein, a person of ordinary skill in the art will recognize that the training module 204 may also use training data sets to train the deep neural network in a supervised or reinforcement learning fashion.

The training data sets may be designed to train one or more deep neural networks of training module 204 to produce different kinds of 3D dental restoration designs 6. For example, to train a deep neural network to produce 3D models of teeth having predefined features (FIG. 1(*i-iii*)) such as predefined recesses on the biting surfaces, a plurality of 2D sketches of the shape of the recesses may be drawn for use. Moreover 2D projections of the surfaces such as top surfaces of a plurality of 3D restorations in a database onto a plane may be obtained and used as input training data. Further, projection of a 3D-restoration's silhouette onto a plane under a certain angle may produce automatically generated sketches for use. 3D models corresponding to the 2D sketches may also be obtained for use as output (target) data in the training dataset, ie. the neural network may an output during training which may be compared to the target/output data of the training dataset. Database 202 may therefore contain different groups of training data sets in an embodiment, one group for each 3D dental restoration geometry type needed, for example.

In an embodiment of the present invention, the training module 204 may train one or more deep neural networks in real-time. In some embodiments, training module 204 may pre-train one or more deep neural networks using training data sets from database 202 such that the computer system 100 may readily use the one or more pre-trained deep neural networks or pre-trained portions (e.g. layers) of deep neural networks to produce 3D dental restoration designs 6. It may then send said 3D dental restoration designs 6 or information about the 3D dental restoration designs 6, preferably automatically and in real time, to a CAD/CAM module 206 for adaptation to a 3D model of a patient's oral cavity and/or for subsequent manufacturing through means such as milling, grinding or additive manufacturing. Other embodiments of the system 200 may include different and/or additional components. Moreover, the functions may be distributed among the components in a different manner than described herein.

Figure 4:
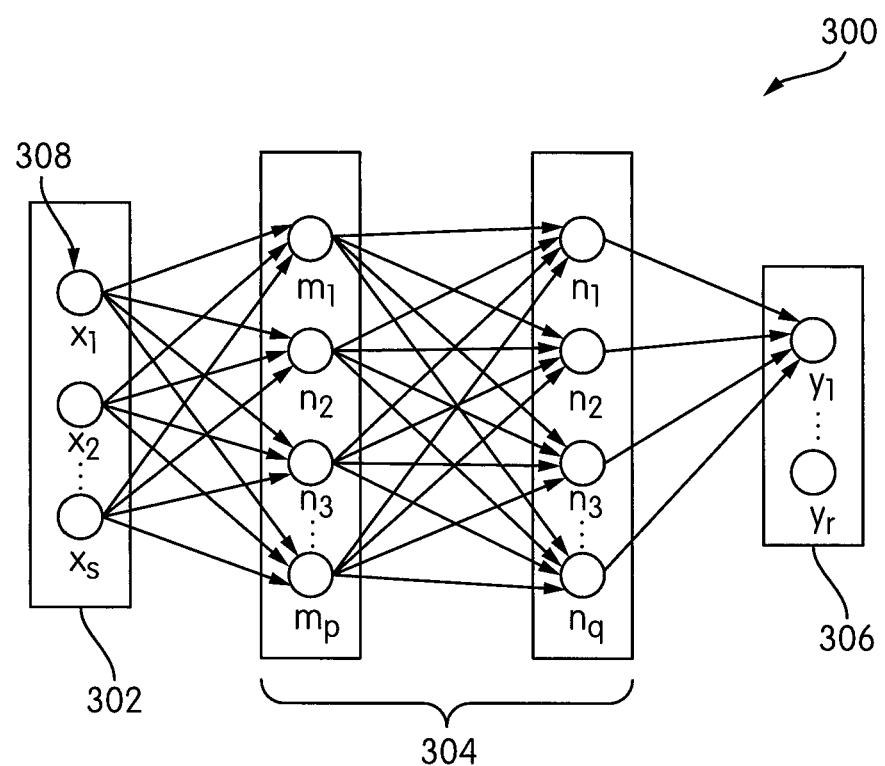
FIG. 4 is a high-level block diagram showing an example structure of a neural network such as a deep neural network according to one embodiment.

FIG. 4 shows a block diagram illustrating an example structure of a neural network such as a deep neural network 300 according to an embodiment of the present invention. It may have several layers including an input layer 302, one or more hidden layers 304 and an output layer 306. Each layer may consist of one or more nodes 308, indicated by small circles. Information may flow from the input layer 302 to the output layer 306, i.e. left to right direction, though in other embodiments, it may be from right to left, or both. For example, a recurrent network may take previously observed data into consideration when processing new data in a sequence 8 (e.g. current images may be segmented taking into consideration previous images), whereas a non-recurrent network may process new data in isolation. A node 308 may have an input and an output and the nodes of the input layer 308 may be passive, meaning they may not modify the data. For example, the nodes 308 of the input layer 302 may each receive a single value (e.g. a pixel value) on their input and duplicate the value to their multiple outputs. Conversely, the nodes of the hidden layers 304 and output layer 306 may be active, therefore being able to modify the data. In an example structure, each value from the input layer 302 may be duplicated and sent to all of the hidden nodes. The values entering the hidden nodes may be multiplied by weights, which may be a set of predetermined numbers associated with each of the hidden nodes. The weighted inputs may then be summed to produce a single number. An activation function (such as a rectified linear unit, ReLU) of the nodes may define the output of that node given an input or set of inputs. Furthermore local or global pooling layers may be used to reduce the dimensions of the data by combining the outputs of neuron clusters at one layer into a single neuron in the next layer In an embodiment according to the present invention, the deep neural network 300 may use pixels of the 2D dental design 2 as input. Herein, the number of nodes in the input layer 302 may be equal to the number of pixels in an 2D dental design 2. In another embodiment according to the present invention, additional feature extraction may be performed on the 2D input sketches prior to forwarding the data to the convolutional neural network. This feature extraction may be e.g. through another neural network, through a color transformation, or through other computer vision algorithms. In yet another embodiment, the feature extraction may be done to categorize features of the 2D input sketches into different sets that may represent characteristics such as structural/physical characteristics of the 3D dental restoration geometry 6.

As discussed, the deep neural network may be a Convolutional Neural Network (CNN), a 3D Generative Adversarial Network (3D-GAN), a Recurrent Neural Network (RNN), a Recurrent Convolutional Neural Network (Recurrent-CNN) or the like. Further, in even yet another embodiment, a non-neural network solution may be achieved by applying a non-neural network feature extraction algorithm such as scale-invariant feature transform (SIFT) (U.S. Pat. No. 6,711,293) or the like to the 2D-input sketches and training a non-neural network regression method such as support vector regression or the like to determine the input of a parametric model such as biogeneric dental designs or other."

Method for Producing 3D Dental Restoration Geometries

Figure 5A:
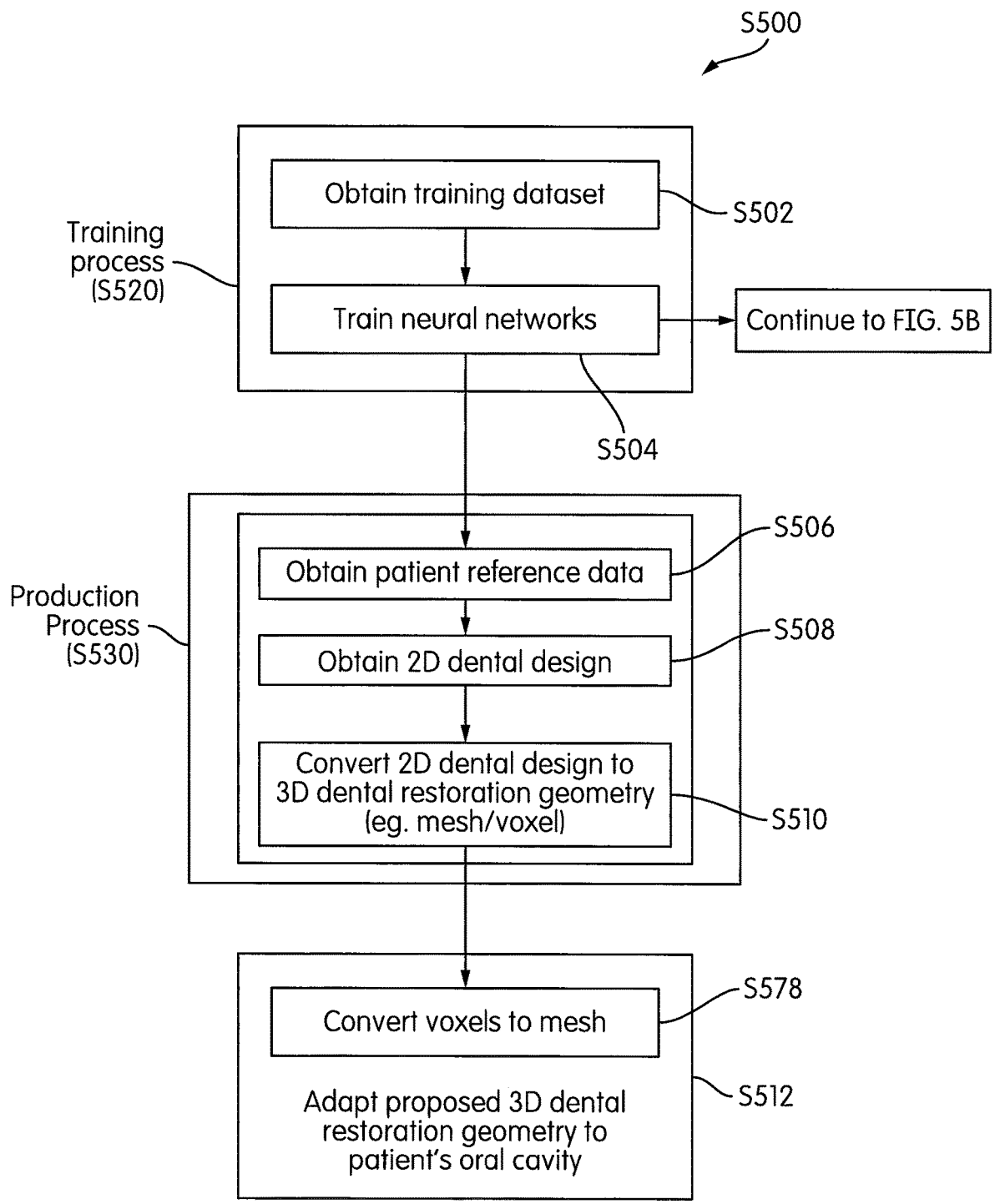
FIG. 5A is a flowchart showing an exemplary method according to an embodiment of the present invention.
Figure 5B:
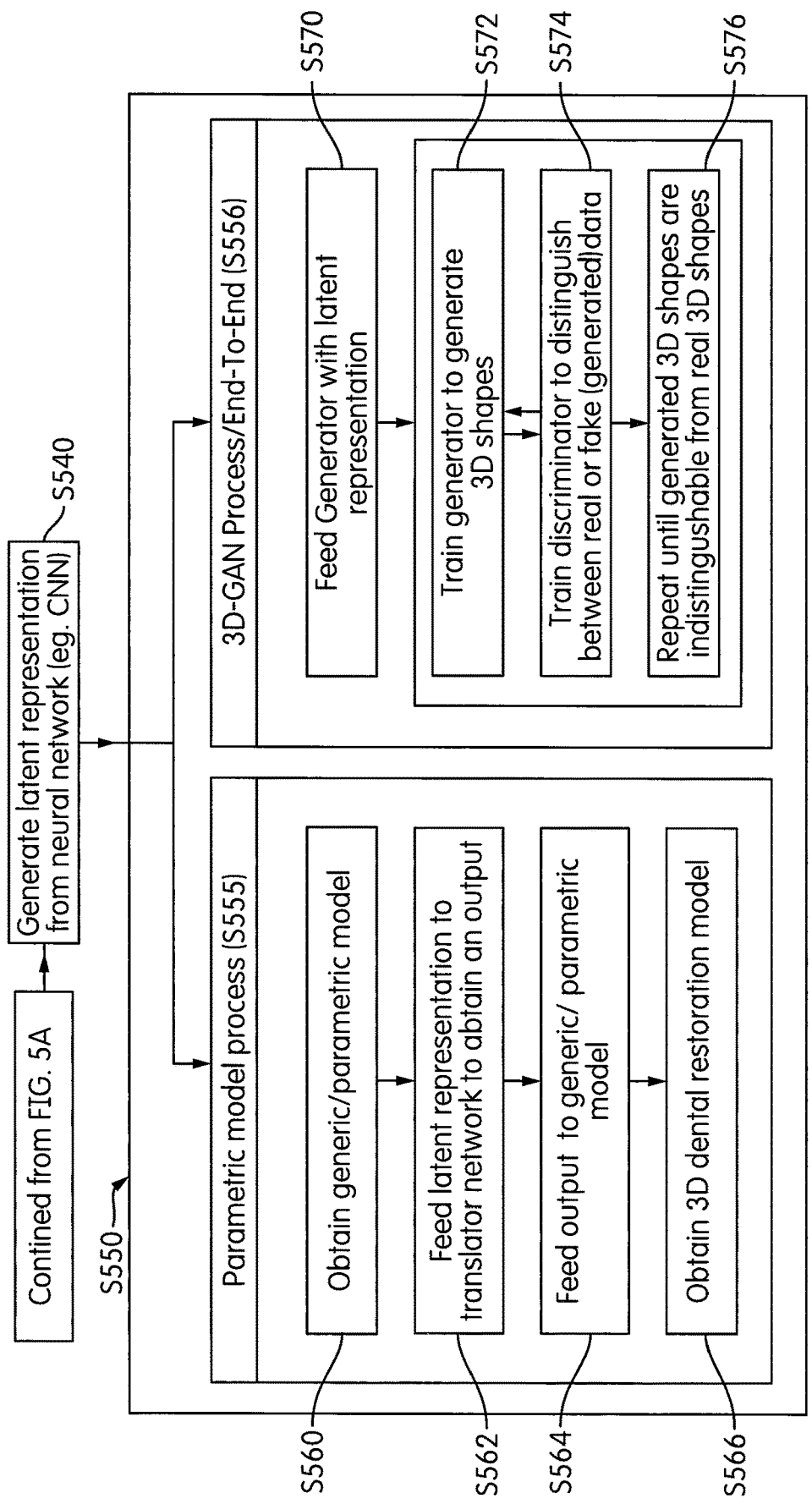
FIG. 5B is a continuation of the flowchart of FIG. 5A showing an exemplary method according to an embodiment of the present invention.

Having described the system 200 of FIG. 2 reference will now be made to FIG. 5A-5B, which show a process S500 in accordance with at least some of the example embodiments herein.

The process S500 may include obtaining a training dataset, Step S502, training the neural network using the training dataset, Step S504, taking a scan of a patient, such as a 3D measurement of a patient's oral cavity, Step S506, obtaining a 2D dental design 2, Step S508, producing a 3D dental restoration geometry 6 using the obtained 2D dental design 2, Step S510 and/or adapting the produced 3D dental restoration geometry 6 to the patient's oral cavity.

The process S500 may be achieved in two major steps: a training step, Step S520 and a production step, Step S530. The various steps in these two major steps of process S500 are described in further detail.

In Steps S506-S508, the system 200 may take as input, a 2D dental design 2, a 3D scan such as a 3D measurement of a patient's cavity, and additional inputs such as one or several photographs of the patient, facebow data, X-ray images etc. These may be used as references for positioning and dimensioning of restoration data. Specifically, face bow data may be used to design occlusal surfaces of the 2D dental design 2 and X-ray data may be used to position implants relative to bone structures. The face bow data may be used to bring mandible and maxilla into the correct relation (in traditional dental workflows using an articulator), i.e. information related occlusion such as occlusal surfaces, static and dynamic contacts etc. may be derived from the face bow data.

The system 200 may achieve Steps S506-S508 by starting the production process S530 through a 2D view on the display unit 128, i.e., through a clinician defining the outlines or features of the dental restorations which are to be produced in relation to the patient's photograph. In doing so, the user may be enabled to take into consideration important anatomical and aesthetically relevant landmarks such as position of eyes, nose, ears, lips, chin and the like. These landmark positions may act as a guideline for clinicians and dental technicians in order to produce a functional and aesthetically pleasing dental restoration, as they may be of value during their dimensioning and positioning.

A further aesthetically relevant factor while designing dental restorations in the anterior positions is the so-called lip support i.e. the inclination of the upper lip. By positioning and inclining the anterior teeth in a dental restoration, the patient's lips (and surrounding tissues) may be moved outward or inward. By using photographs from a side view, a user such as a dental technician or clinician may judge the amount of that support needed and incorporate that into the 2D dental design 2. As this may not be discerned in frontal views, it may necessitate the use of photographs taken from the sides. Once the clinician is finished designing the 2D dental design 2, the system 200 may automatically propose (Step S510) a suitable a 3D shape for one or more dental restorations that adheres to the 2D dental design 2. This proposal may also be adapted in Step S512 to anatomical constraints known to the system 200 from the given 3D-scans(x-rays and optical measurements) such as position on the jaws, neighboring tooth shapes and sizes, contact points to antagonists (if present) and fissures or similar features of neighboring existing teeth (if present). Further, the proposal is based on the training process Step S520.

Turning now to the training process Step S520, each pair of a 2D dental design 2 and 3D dental restoration geometry 6 may form an example for a correspondence to be obtained, Step S502, and used for training. Several 2D dental designs 2 may exist for each 3D dental restoration geometry 6 in the training dataset. As discussed, the 2D dental designs 2 may be human-made drawings or automatically generated sketches (e.g. by projecting a 3D-restoration's silhouette onto the plane under a certain angle). They may be in the form of 2D raster data (pixel images) and may be grayscale, black/white or color images. In an embodiment herein, the pixels of the 2D dental design 2 may not be labeled. Instead the training data may represent a mapping from one such 2D sketch to a 3D restoration geometry. The neural network model obtained after training may then be used to generate 3D designs using new 2D-sketches as input which sketches have not been part of the training data set.

Figure 6:
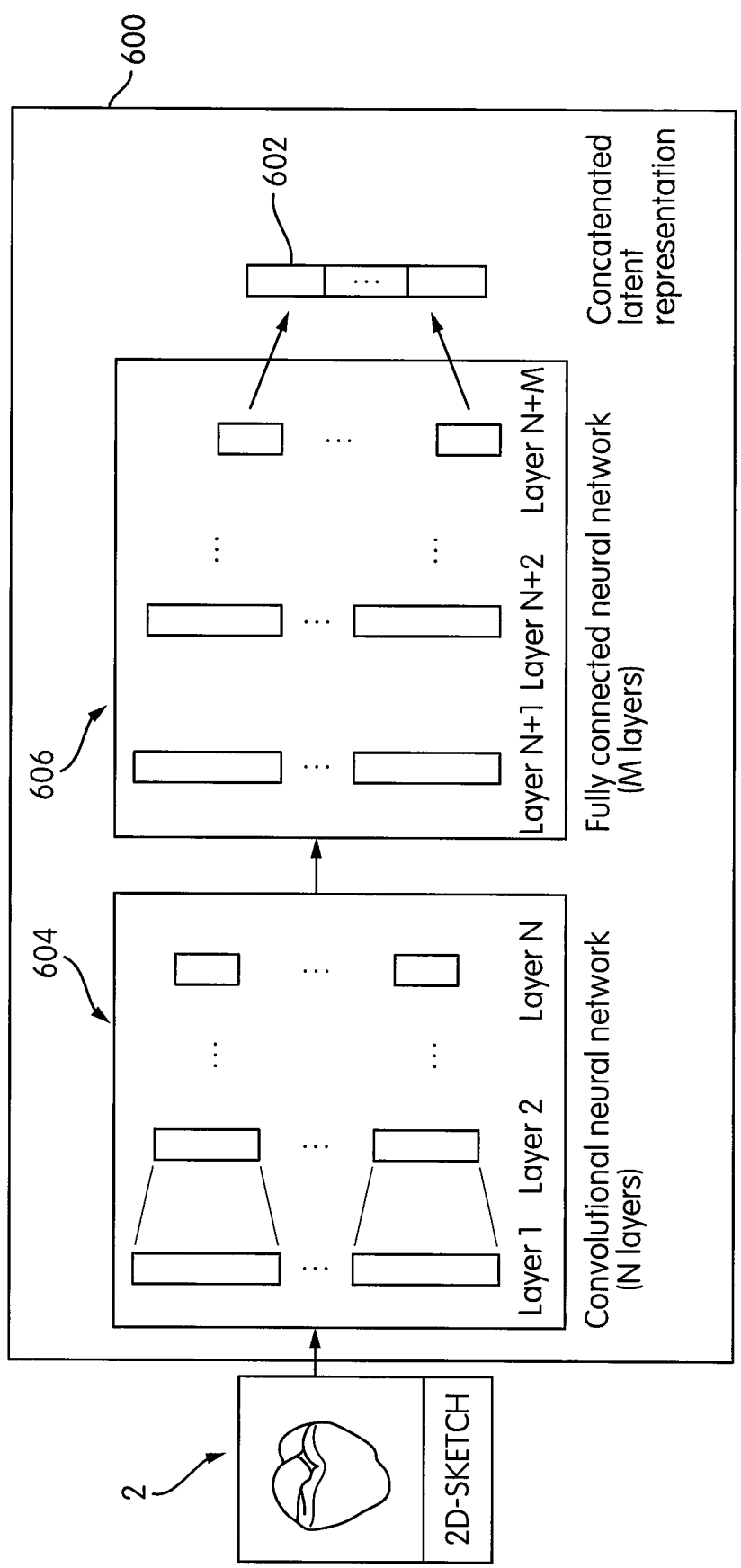
FIG. 6 is a block diagram illustrating the production of a latent representation according to an embodiment of the present invention.

Step S504 of the training process may model the mapping between a 2D dental design 2 and a 3D dental restoration model 6 in different ways. Referring now to FIG. 6, a first neural network such as a deep convolutional neural network 600 may be used to translate a 2D dental design 2 into a numerical representation, which is referred to hereinafter a "latent representation" 602. The latent representation 602 may be a vector and may contain all essential information from the 2D dental design 2 to enable subsequent generation of a 3D dental restoration model which adheres to the intended design drawn by the clinician.

The latent representation 602 may not be interpretable to a human being but may rather be an abstract numerical representation of the 2D dental design 2. Thus the process of generating the latent representation 602 can be thought of as a form of lossy data compression. During the training phase, the system may ensure that the latent representation will contain information required to generate 3D-dental restoration geometries which are aligned with a human operator's intention when the system is presented with corresponding 2D-input sketches. One way to mathematically describe the latent representation may be the following: Let the input data be described by a random variable. Consequently, the latent representation is also a vector-, matrix- or tensor-tensor valued random variable of fixed dimension, the number of its dimensions being lower or equal to the number of parameters of the 2D-input sketches. The computation rule for this latent representation which is implicitly constructed during the training process may be one that maximizes the mutual information between the input and the latent representation.

This first part Step S540 of the training step, Step S504 may apply several layers of shared weights to pixels of the 2D dental design 2 in one or more convolutional layers 604, followed by a number of fully connected layers 606. The weights may be computed so as to minimize a loss function between the system's output and the training targets in the training data set. All values from the final layers may be concatenated into one vector, having a length that may preferably be substantially smaller than the number of pixels in the input 2D dental design 2, thus forming the latent representation 602, which may be subsequently used to generate the 3D dental restoration geometry 6 as discussed hereinafter.

In creating the 3D dental restoration, the latent representation 602 may be expanded/upsampled (Step S550) to a 3D restoration mesh using a second neural network. Herein a 3D-GAN/end-to-end method (Step S556) or a translator network with a parametric model method (Step S555) may be employed. After the first part, Step S540 of the training step, (from 2D sketch image to latent representation) learns the correspondence by optimization, a second part/upsampling step, Step S550 of the training step generates a 3D dental restoration geometry 6 from the latent representation 602.

In Step S555, a parametric implementation model may be used. U.S. Pat. No. 9,672,444 B2 entitled "Method for producing denture parts or for tooth restoration using electronic dental representations", by Albert Mehl, discloses biogeneric dental designs and is incorporated by reference herein in its entirety, as if set forth fully herein.

In U.S. Pat. No. 9,672,444 B2, sample scans of multiple teeth from a tooth library may be averaged to form an average tooth model, Principal Component Analysis (PCA) may be performed on the difference between the average tooth model and the sample scans to obtain the most important principal components (those having high variance proportions) that may be combined to get a generic tooth model, said generic tooth model representing the biogeneric dental designs. These most important principal components may have factors that may be modified to observe a corresponding change in said generic tooth model as illustrated in FIG. 18 of U.S. Pat. No. 9,672,444 B2.

Figure 7:
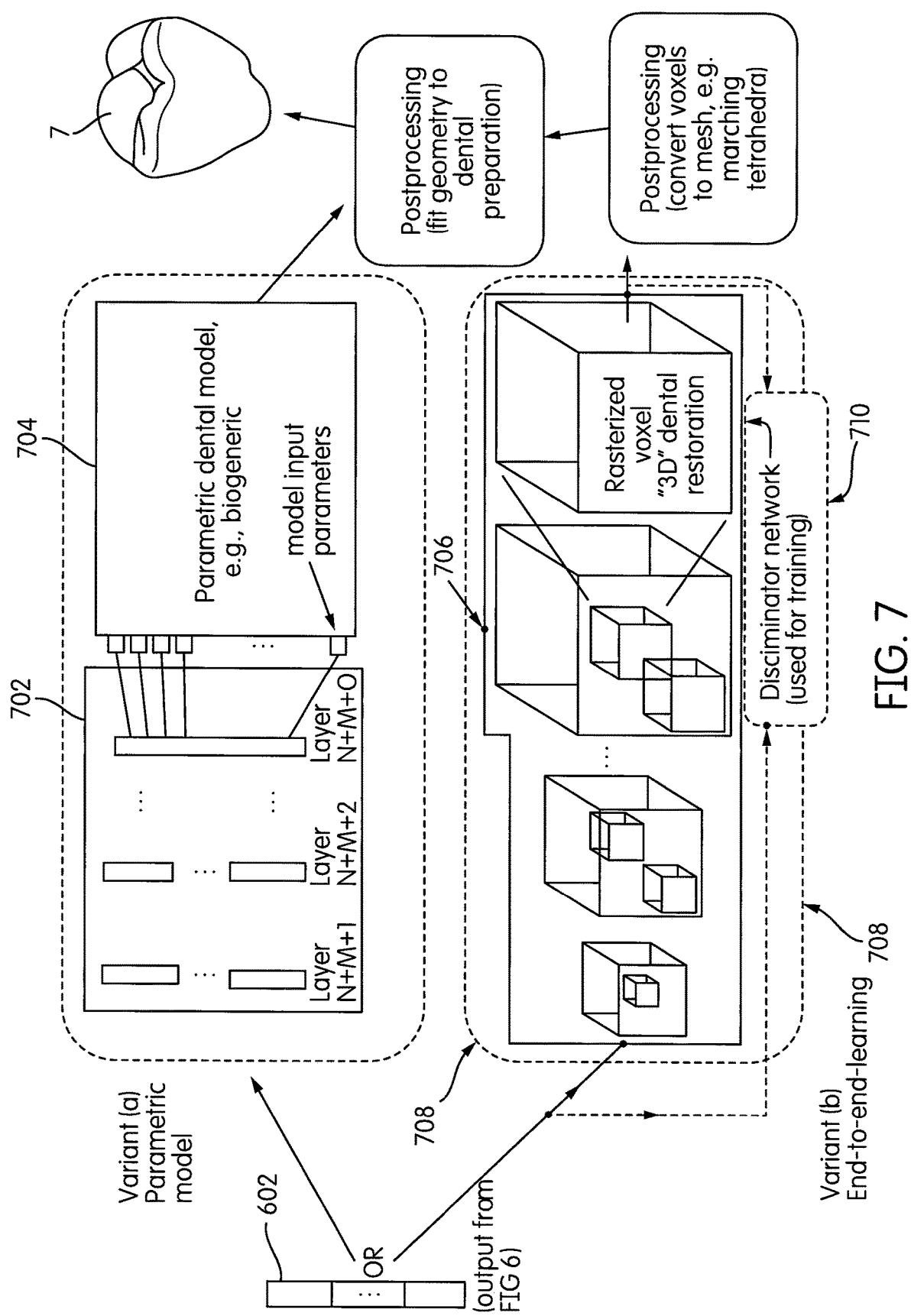
FIG. 7 is a block diagram showing embodiments of the present invention.

In Step S560, such a generic model (hereinafter referred to as a parametric model 704, FIG. 7) may be obtained. Assuming that said parametric model 704 has some fixed number of input parameters, the latent representation 602 may be translated into the input parameters of the parametric model 704 using a translation unit 702. Herein, a further neural network (the translation unit 702), which has the same number of input units as the length of the latent representation 602, and the same number of output units as the number of input parameters of the parametric model 704 may be employed in the upsampling step, Step S550 of the training step. The translation unit may be any neural network such as a CNN, a fully connected multilayer perceptron, a recurrent neural network or the like. By feeding the latent representation into this translator network (Step S562), and the output to the parametric model 704 (Step S564), the system will output 3D dental restoration geometries 6 (Step S566). This may be represented in the form a mesh structure suitable for dental CAD workflows and may subsequently be adapted into a final digital dental restoration 7, after the training, to fit inside the individual patient's oral cavity, Step S512.

In another embodiment, a 3D-GAN 708 may be trained to create the 3D dental restoration geometries from the latent representation 602 as shown in the "end-to-end" process, Step S556. In contrast to the process using a parametric model 706 (Step S555), said "end-to-end" machine learning modeling process Step S556, may be used to directly create 3D outputs from input 2D dental designs 2.

This may be implemented using a 3D-GAN 708 that may comprise a generator 706, which may be trained to generate/produce structured 3D data (e.g. voxels or octrees) data, and a discriminator 710, which may be used during the training phase of the model to evaluate the output of the generator 706. During the training phase, latent representation 602 may be fed to the generator 706 in Step S572 and the generator 706 may be trained to attempt to generate 3D shapes using the latent representation (Step S572), such that the generated 3D shapes are indistinguishable from real dental restorations/real 3D dental design geometries. In an embodiment herein, these shapes may be in the form of 3D meshes.

These generated 3D shapes as well as real 3D shapes may be fed to the discriminator. Simultaneously during the training, the discriminator 710 may determine whether the 3D shapes are real or generated, Step S574 in order to reach a best possible discrimination rate between generated and real data. Herein, the output of the discriminator may be fed back to the generator 706 to re-train it and the cycle may be repeated a number of times, Step S576, until the generated 3D shapes are indistinguishable from the real 3D shapes. In an embodiment of the present invention, the generator network may produce structured 3D output data (e.g. voxels or octrees) in which every voxel or other element is labeled as a restoration data or as a non-restoration data.

In another embodiment herein, only the generator part of the 3D-GAN may be used after the training has completed.

Since the output of the generator network may comprise of 3D-raster data, this data may be transformed into a mesh-representation suitable for dental CAD workflows, Step S578. This can be achieved using, for example, the marching tetrahedral algorithm, the marching cube algorithm or the like. The mesh structure may then subsequently be adapted into a final digital dental restoration 7 to fit inside the individual patient's oral cavity, Step S512. Of course other structures may be realized by persons of ordinary skill in the art in light of this specification.

In Step S512, 3D dental restoration geometries 6 obtained from the parametric model or 3D-GAN process may be adapted to a specific patient's dental situation to produce a final digital dental restoration 7 by considering anatomical constraints including, but not limited to, the patient's dental preparation boundary, geometry of a connecting element (prepared stump, implant or implant suprastructure/superstructure), contacts to adjacent natural or restored teeth, contacts to antagonist(s), alignment of anatomical features such as fissures and dynamic contacts (articulation). The dental restoration geometry 6 may thus be linked to the available scan(s) of a patient's dental situation by replicating the shape of the preparation line (margin) and possibly accommodating a spacer and/or instrument geometries (in case of subtractive manufacturing).

Therefore a 3D dental restoration geometry 6 may be augmented on its basal side in order to fit to the underlying connection such as a stump, implant, TiBase, implant suprastructure, or the like. It may then be oriented to align with the patient's dental situation. Herein, it may be oriented such that its occlusal surface lies on the patient's occlusal plane. The orientation may also be automatically proposed by a dental CAD software or manually specified by the user of a dental CAD software.

The 3D dental restoration geometry 6 may then be scaled to fill a provided space in order to reach a desired contact situation to its neighboring teeth/restorations.

Further, 3D dental restoration geometry 6 may be adapted to be in occlusion with the opposing jaw. Herein, the geometry of the restoration's occlusal surface is adapted to reach a contact situation which the opposing tooth/teeth/ restoration/restorations to resemble a natural situation. In an embodiment of the present invention, this may be implemented using a machine learning algorithm.

Using the training data described above, the system 200 may be trained using, for example, a stochastic gradient descent. When using the parametric model process (Step S555) for geometry generation the parametric model 704 may be used in a black box fashion during training: The output of the parametric model may be used to compute an error (or loss) measure with respect to the training data. Suitable error functions include mean square and cross entropy error functions. In order to evaluate the error, a deviation between a surface generated by the model and a surface of the training set model may be used. When using end-to-end process, Step S556, the system 200 may be trained using stochastic gradient descent to maximize the probability of generating 3D-geometries that are aligned with a human operator's conveyed intention when drawing a 2D-sketch Further, batch mini batches may be used here.

In yet another embodiment of the present invention the system 200 may be trained or further trained on a specific user's drawing style. Since different users may have different drawing styles, it may be desirable to adapt the system to a specific user's style. Hence, the system or neural networks may be further trained on a specific user's 2D-sketches and generated restorations so that production of 3D dental restoration geometries 6 may better match the user's drawing style. Further the last m layers of an n-layer network, where m≤n may be retrained using the specific users additional/novel sketch-3D restoration pairs.

In even yet another embodiment, a 2D sketch drawn by a user to produce a 3D dental restoration geometry 6 may be updated to generated corresponding changes to the 3D dental restoration geometry preferably in real time. This may be repeated until a desirable 3D shape is achieved. In another embodiment, multiple 2D sketches may be used to create a 3D dental restoration geometry 6.

After the production of the final digital dental restoration 7, it may be manufactured using CAD/CAM system 206. Moreover, it may be fed into a dental CAD workflow, thus allowing any processing of the shape that may be needed. The shapes produced by the present invention are suitable for traditional crown or telescope or framework design, for implant-based dental restorations and removable dental restorations such a supra-structures or dentures and the like.

It will be understood by a person of ordinary skill in the art, in light of this description that other computational methods stemming from the field of machine learning may be implemented using e.g. convolutional neural networks, other deep learning methods, or other suitable algorithms/methods to build generative models from training data.

Computer System for Producing 3D Dental Restoration Geometries

Figure 8:
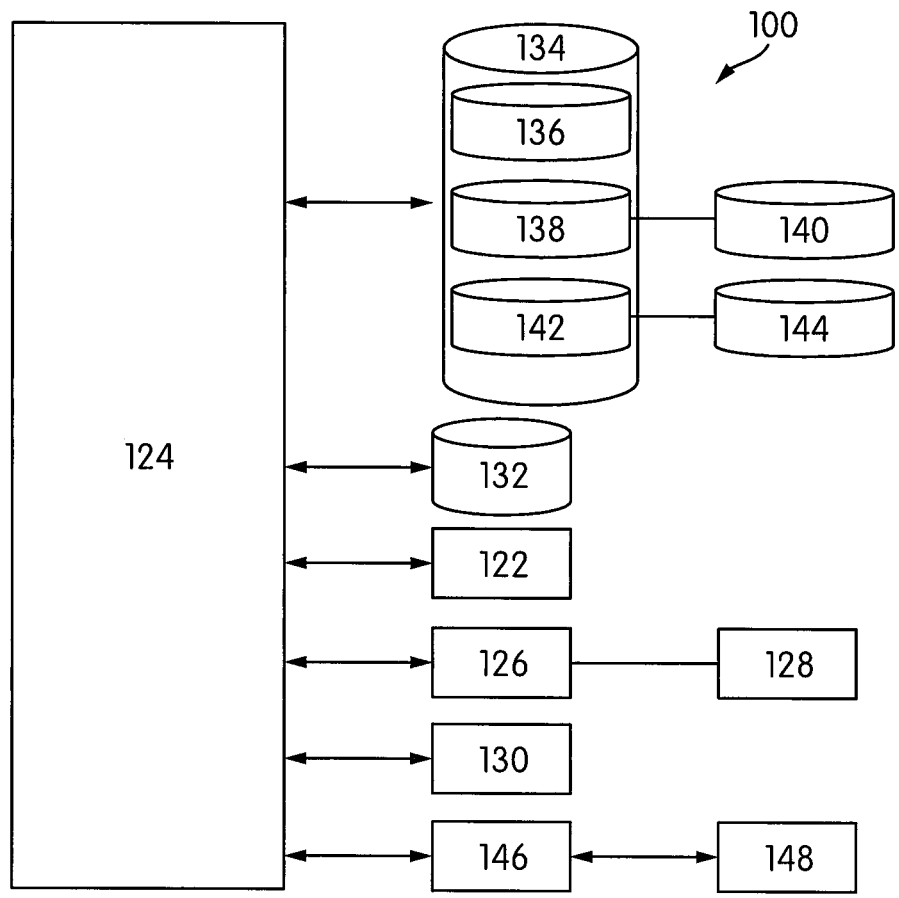
FIG. 8 is a block diagram showing a computer system according to an exemplary embodiment of the present invention.

Having described the process S500 of FIG. 5A-5B reference will now be made to FIG. 8, which shows a block diagram of a computer system 100 that may be employed in accordance with at least some of the example embodiments herein. Although various embodiments may be described herein in terms of this exemplary computer system 100, after reading this description, it may become apparent to a person skilled in the relevant art(s) how to implement the invention using other computer systems and/or architectures.

The computer system 100 may include or be separate from the training module 204, database 202 and/or CAD/CAM System 206. The modules may be implemented in hardware, firmware, and/or software. The computer system may also include at least one computer processor 122, user interface 126 and input unit 130. The input unit 130 in one exemplary embodiment may be used by the dentist along with a display unit 128 such as a monitor to send 2D sketches and/or instructions or requests about creating 3D dental restoration geometries 6. In another exemplary embodiment herein, the input unit 130 is a finger or stylus to be used on a touchscreen interface display device (not shown). The input unit 130 may alternatively be a gesture recognition device, a trackball, a mouse or other input device such as a keyboard or stylus. In one example, the display unit 128, the input unit 130, and the computer processor 122 may collectively form the user interface 126.

The computer processor 122 may include, for example, a central processing unit, a multiple processing unit, an application-specific integrated circuit ("ASIC"), a field programmable gate array ("FPGA"), or the like. The processor 122 may be connected to a communication infrastructure 124 (e.g., a communications bus, or a network). In an embodiment herein, the processor 122 may receive a request for creating 3D dental restoration geometries 6 and may automatically create said geometries in digital and physical form using the training module 204, database 202 and CAD/CAM System 206. The processor 122 may achieve this by loading corresponding instructions stored in a non-transitory storage device in the form of computer-readable program instructions and executing the loaded instructions.

The computer system 100 may further comprise a main memory 132, which may be a random access memory ("RAM") and also may include a secondary memory 134. The secondary memory 134 may include, for example, a hard disk drive 136 and/or a removable-storage drive 138. The removable-storage drive 138 may read from and/or write to a removable storage unit 140 in a well-known manner. The removable storage unit 140 may be, for example, a floppy disk, a magnetic tape, an optical disk, a flash memory device, and the like, which may be written to and read from by the removable-storage drive 138. The removable storage unit 140 may include a non-transitory computer-readable storage medium storing computer-executable software instructions and/or data.

In further alternative embodiments, the secondary memory 134 may include other computer-readable media storing computer-executable programs or other instructions to be loaded into the computer system 100. Such devices may include a removable storage unit 144 and an interface 142 (e.g., a program cartridge and a cartridge interface); a removable memory chip (e.g., an erasable programmable read-only memory ("EPROM") or a programmable read-only memory ("PROM")) and an associated memory socket; and other removable storage units 144 and interfaces 142 that allow software and data to be transferred from the removable storage unit 144 to other parts of the computer system 100.

The computer system 100 also may include a communications interface 146 that enables software and data to be transferred between the computer system 100 and external devices. Such an interface may include a modem, a network interface (e.g., an Ethernet card, a wireless interface, a cloud delivering hosted services over the internet, etc.), a communications port (e.g., a Universal Serial Bus ("USB") port or a FireWire® port), a Personal Computer Memory Card International Association ("PCMCIA") interface, Bluetooth®, and the like. Software and data transferred via the communications interface 146 may be in the form of signals, which may be electronic, electromagnetic, optical or another type of signal that may be capable of being transmitted and/or received by the communications interface 146. Signals may be provided to the communications interface 146 via a communications path 148 (e.g., a channel). The communications path 148 may carry signals and may be implemented using wire or cable, fiber optics, a telephone line, a cellular link, a radio-frequency ("RF") link, or the like. The communications interface 146 may be used to transfer software or data or other information between the computer system 100 and a remote server or cloud-based storage.

One or more computer programs or computer control logic may be stored in the main memory 132 and/or the secondary memory 134. The computer programs may also be received via the communications interface 146. The computer programs may include computer-executable instructions which, when executed by the computer processor 122, cause the computer system 100 to perform the methods as described herein.

In another embodiment, the software may be stored in a non-transitory computer-readable storage medium and loaded into the main memory 132 and/or the secondary memory 134 of the computer system 100 using the removable-storage drive 138, the hard disk drive 136, and/or the communications interface 146. Control logic (software), when executed by the processor 122, causes the computer system 100, and more generally the system for detecting scan interferences, to perform all or some of the methods described herein.

Implementation of other hardware and software arrangement so as to perform the functions described herein will be apparent to persons skilled in the relevant art(s) in view of this description.

What is claimed is:

1. A computer implemented method for producing a three-dimensional (3D) dental restoration geometry from a two-dimensional (2D) dental design, the method comprising:
    receiving, by one or more computing devices, a 2D dental design having design constraints that represent defined properties of said 3D dental restoration geometry;
    using a first trained neural network to convert the 2D dental design into a latent representation that has information about said defined properties of the 3D dental restoration geometry;
    upsampling the latent representation to automatically generate the 3D dental restoration geometry by using the latent representation as input to a second trained neural network and converting said latent representation into a 3D shape that has corresponding properties that adhere to said design constraints.

2. The method of claim 1 further comprising adapting the 3D dental restoration geometry into a final digital dental restoration to fit inside a patient's oral cavity based on anatomical constraints obtained from 3D scans of the patient.

3. The method of claim 2, further comprising manufacturing a physical dental restoration from the final digital dental restoration using a computer-aided design/computer-aided manufacturing (CAD/CAM) system.

4. The method of claim 1, wherein the defined properties include cusps, ridges, fissures, bifurcations, tooth shape and tooth texture.

5. The method of claim 1, wherein the first neural network is a convolutional neural network.

6. The method of claim 1, wherein the second neural network is an additional neural network selected from a convolutional neural network, a recurrent neural network, and a fully connected multilayer perceptron or wherein the second neural network is a three-dimensional generative adversarial neural network (3D-GAN).

7. The method of claim 5 further comprising using an output of the additional neural network as an input to a parametric model wherein the convolutional neural network has a same number of input units as a length of the latent representation, and another same number of output units as a number of input parameters of the parametric model.

8. The method of claim 1 wherein the 3D dental restoration geometry is generated as a 3D triangular mesh or a 3D rasterized data.

9. The method of claim 1, wherein the 2D dental design is a 2D sketch recorded in an analog or digital way.

10. The method according to claim 1, further comprising:
    training the first and second neural networks using the one or more computing devices and a plurality of training images in a training dataset, to map a 2D training image having design constraints to a 3D training mesh,
    wherein the first neural network is trained to convert the 2D training image into a latent representation that has information about defined properties of the 3D training mesh, and
    the second neural network is trained to upsample the latent representation to automatically generate the 3D training mesh such that it has corresponding properties that adhere to said design constraints of said 2D training image.

11. The method of claim 10, further comprising retraining the first and second neural networks using 2D training images of a specific user to subsequently generate 3D dental restoration geometries that match or substantially match a drawing style of the specific user.

12. A non-transitory computer-readable storage medium storing a program which, when executed by a computer system, causes the computer system to perform a procedure comprising:
    receiving, by one or more computing devices, a two-dimensional (2D) dental design having design constraints that represent defined properties of a 3D dental restoration geometry;
    using a first trained neural network to convert the 2D dental design into a latent representation that has information about said defined properties of the 3D dental restoration geometry;
    upsampling the latent representation to automatically generate the 3D dental restoration geometry by using the latent representation as input to a second trained neural network and converting said latent representation into a 3D shape that has corresponding properties that adhere to said design constraints.

13. A system for producing a three-dimensional (3D) dental restoration geometry from a two-dimensional (2D) dental design, the system comprising a processor configured to:
    receive, by one or more computing devices, a 2D dental design having design constraints that represent defined properties of said 3D dental restoration geometry;
    use a first trained neural network to convert the 2D dental design into a latent representation that has information about said defined properties of the 3D dental restoration geometry;
    upsample the latent representation to automatically generate the 3D dental restoration geometry by using the latent representation as input to a second trained neural network and converting said latent representation into a 3D shape that has corresponding properties that adhere to said design constraints.

14. The system of claim 13, wherein the processor is further configured to adapt the 3D dental restoration geometry into a final digital dental restoration to fit inside a patient's oral cavity based on anatomical constraints obtained from 3D scans of the patient.

15. The system of claim 13, wherein the first neural network is a convolutional neural network.

16. The system of claim 13, wherein the second neural network is an additional neural network selected from a convolutional neural network, a recurrent neural network, and a fully connected multilayer perceptron or wherein the second neural network is a three-dimensional generative adversarial neural network (3D-GAN).

17. The system of claim 13 wherein the 3D dental restoration geometry is a 3D triangular mesh or a 3D rasterized data.

18. The system of claim 13, wherein the 2D dental design is a 2D sketch recorded in an analog or digital way.

19. A computer implemented method for producing a three-dimensional (3D) dental restoration geometry from one or more two-dimensional (2D) dental designs, the method comprising:
receiving, by one or more computing devices, one or more 2D dental designs having design constraints that represent defined properties of said 3D dental restoration geometry;
using a first trained neural network to convert the one or more 2D dental designs into a latent representation that has information about said defined properties of the 3D dental restoration geometry;
upsampling the latent representation to automatically generate the 3D dental restoration geometry by using the latent representation as input to a second trained neural network and converting said latent representation into a 3D shape that has corresponding properties that adhere to said design constraints.

20. A computer implemented method for producing one or more three-dimensional (3D) dental restoration geometries from a two-dimensional (2D) dental design, the method comprising:
receiving, by one or more computing devices, a 2D dental design that has design constraints that represent defined properties of said one or more 3D dental restoration geometries;
using a first trained neural network to convert the 2D dental design into a latent representation that has information about said defined properties of the one or more 3D dental restoration geometries;
upsampling the latent representation to automatically generate the one or more 3D dental restoration geometries by using the latent representation as input to a second trained neural network and converting said latent representation into a 3D shape that has corresponding properties that adhere to said design constraints.

* * * * *